United States Patent [19]

Conkling et al.

[11] Patent Number: 5,459,252
[45] Date of Patent: Oct. 17, 1995

[54] ROOT SPECIFIC GENE PROMOTER

[75] Inventors: Mark A. Conkling, Fuquay-Varina, N.C.; Yuri T. Yamamoto, New Haven, Conn.

[73] Assignee: North Carolina State University, Raleigh, N.C.

[21] Appl. No.: 234,939

[22] Filed: Apr. 28, 1994

Related U.S. Application Data

[63] Continuation of Ser. No. 649,564, Jan. 31, 1991, abandoned.

[51] Int. Cl.⁶ .......................... C07H 21/04; C12N 15/11; C12N 15/29; A01H 5/00
[52] U.S. Cl. ................. 536/24.1; 435/240.4; 435/252.3; 435/320.1; 800/205; 935/35; 935/36
[58] Field of Search ....................... 536/24.1; 435/240.4, 435/252.3, 320.1; 800/205; 935/35, 36; 514/44

[56] References Cited

U.S. PATENT DOCUMENTS

| | | | |
|---|---|---|---|
| 4,943,674 | 7/1990 | Houck et al. | 800/205 |
| 5,177,308 | 1/1993 | Barton et al. | 800/205 |
| 5,229,292 | 7/1993 | Stock et al. | 435/252.34 |

FOREIGN PATENT DOCUMENTS

WO91/13992  9/1991  WIPO.

OTHER PUBLICATIONS

Y. Yamamoto et al., *J. Cell. Biochem.* 13D (Supp.), 313 (1989).
Conkling et al 1990 (Jul.) Plant Physiol 93: 1203–1211.
Lerner et al 1989 Plant Physiol 91: 124–129.
Evans et al 1988 Mol. Gen. Genet. 214: 153–157.
Yamamoto et al 1991 The Plant Cell 3: 371–382.
Yamamoto et al 1990 Nucleic Acids Research 18: 7449.
Sanford 1988 Trends in Biotechnology 6: 299–302.
Yamamoto et al 1989 PhD Thesis, Genetics Dept., N.C. State Univerisity, Raleigh N.C.

*Primary Examiner*—Patricia R. Moody
*Attorney, Agent, or Firm*—Bell, Seltzer, Park & Gibson

[57] ABSTRACT

Disclosed is an isolated DNA molecule comprising a DNA promoter sequence, the RB7 promoter sequence, which is capable of directing root-specific transcription of a downstream structural gene in a plant cell. Also disclosed is a DNA construct comprising an expression cassette, which construct comprises, in the 5' to 3' direction, a promoter of the present invention and a structural gene such a gene coding for an insect toxin positioned downstream from the promoter and operatively associated therewith. Transformed plants, such as tobacco plants, which comprise transformed plant cells which contain a heterologous DNA construct comprising an expression cassette as described above are also disclosed.

13 Claims, 2 Drawing Sheets

ROOT SPECIFIC GENE PROMOTER

This invention was made with government support under Grant No. DMB-8811077-01 from the National Science Foundation. The government may have certain rights to this invention. This is a continuation of application Ser. No. 07/649,564 filed on Jan. 31, 1991 (now abandoned).

FIELD OF THE INVENTION

This invention relates to tissue-specific gene promoters, and particularly relates to a promoter which is active in the roots of plants.

BACKGROUND OF THE INVENTION

A promoter is a DNA sequence which flanks a structural gene, and to which RNA polymerase must bind if it is to transcribe the flanking structural gene into messenger RNA. One example of a plant promoter is the promoter found flanking the gene for the small subunit ribulose-1,5-bisphosphate carboxylase in Petunia. See U.S. Pat. No. 4,962,028. Another example is the promoter which comprises the 5' flanking region of the wheat Em gene. See EPO Appln. No. 335528. Still another example is the stress-inducible regulatory element disclosed in EPO Appln. No. 0 330 479.

Despite their important role in plant development, relatively little work has been done on the regulation of gene expression in roots. In part the deficiency results from a paucity of readily indentifiable, root-specific biochemical functions whose genes may be easily cloned and studied. Evans et al., Mol. Gen. Genet. 214, 153–157 (1988), tried unsuccessfully to isolate root-specific cDNA clones from pea, concluding that root-specific mRNA species (if present) are only present at a very low level of abundance in the root mRNA population. Fuller et al., Proc. Natl. Acad. Sci. USA 80, 2594–2598 (1983), have cloned and characterized a number of root nodule-specific genes. Comparisons of the DNA sequences 5' of the initiation of transcription reveal a repeated octanucleotide present in the three genes examined. Unfortunately, the lack of efficient transformation/regeneration systems for most Leguminaceae has hampered the functional analysis of such cis-acting sequences. Bogusz et al., Nature 331, 178–180 (1988), isolated a haemoglobin gene expressed specifically in roots of non-nodulating plants by its homology with the haemoglobin gene of closely related, nodulating species. Keller and Lamb, Genes & Dev. 3, 1639–1646 (1989), isolated a gene encoding a cell wall hydroxyproline rich glycoprotein expressed during lateral root initiation. Lerner and Raikhel, Plant Physiol. 91, 124–129 (1989), recently reported the cloning and characterization of a barley root-specific lectin.

Imparting useful traits to plants by expressing foreign genes in plants through genetic engineering techniques will require the availability of a variety of tissue-specific promoters so that new traits can be expressed in the appropriate plant tissues. The present invention is based upon our continuing investigations in connection with this problem.

SUMMARY OF THE INVENTION

A first aspect of the present invention is an isolated DNA molecule comprising a DNA promoter sequence, the RB7 promoter sequence, which is capable of directing root-specific transcription of a downstream structural gene in a plant cell. The promoter sequence may be selected from the group consisting of the tobacco RB7 promoter and DNA sequences which are at least about 75 percent homologous to a 50 base segment of the Tobacco RB7 promoter capable of directing root-specific transcription of a downstream structural gene in a plant cell.

A second aspect of the present invention is a DNA construct comprising an expression cassette, which construct comprises, in the 5' to 3' direction, an RB7 promoter and a structural gene positioned downstream from the promoter and operatively associated therewith.

A third aspect of the present invention is transformed plants comprising transformed plant cells. The transformed plant cells contain a heterologous DNA construct comprising an expression cassette as described above.

The foregoing and other aspects of the present invention are explained in detail in the discussion set forth below.

DETAILED DESCRIPTION OF THE INVENTION

Figure 1:
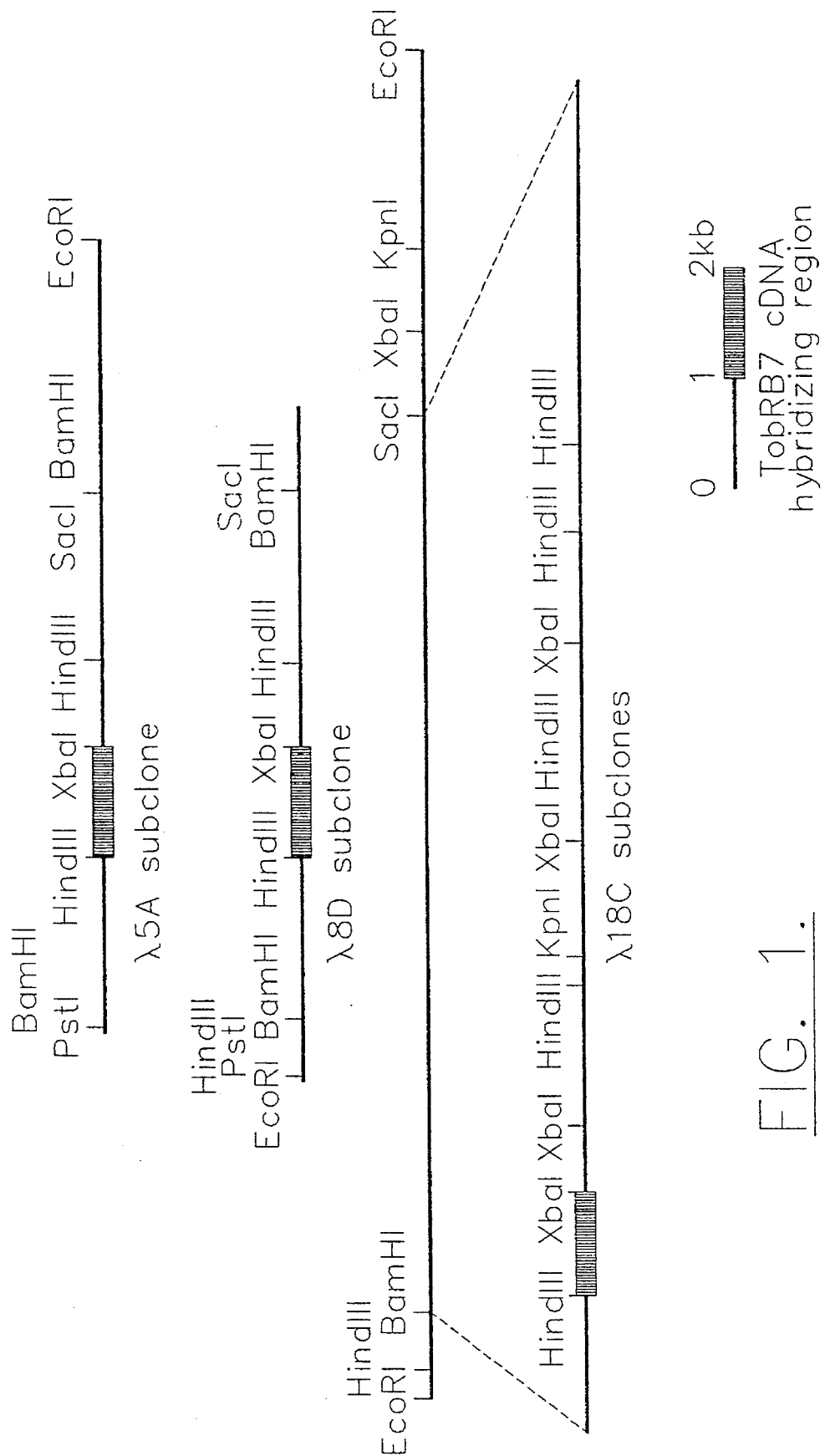
FIG. 1 shows restriction maps of genomic clones hybridizing to the root-specific cDNA clone TobRB7. Genomic clones were restriction mapped for BamHI (B), HindIII (H), PstI (P), EcoRI (R), and SalI (S). Regions hybridizing to the root specific cDNA clone RB7 are shown under the bars.

Specific examples of promoters of the present invention are DNA molecules which have a sequence corresponding to that shown in SEQ ID NO: 3, SEQ ID NO: 4, SEQ ID NO: 5, SEQ ID NO: 6, SEQ ID NO: 7, SEQ ID NO: 8, and SEQ ID NO: 9, all of which are discussed in greater detail below. It will be apparent that other fragments from the Tobacco RB7 5' flanking region, longer or shorter than the foregoing, or with minor additions, deletions, or substitutions made thereto, can be prepared which will also carry the Tobacco RB7 promoter, all of which are included within the present invention. A further aspect of the present invention includes promoters isolated from other tobacco genes, or from plants other than tobacco as set forth below, which are homologous to the tobacco RB7 promoter and are capable of directing root-specific transcription of a downstream structural gene in a plant cell.

RB7 promoter sequences may be obtained from other plant species by using TobRB7 structural gene segments as probes to screen for homologous structural genes in other plants by DNA hybridization under low stringency conditions. Alternatively, regions of the TobRB7 structural gene which are conserved among species could be used as PCR primers to amplify a longer segment from a species other than Tobacco, and that longer segment used as a hybridization probe (the latter approach permitting higher stringency screening). Examples of plant species which may be used in accordance with the foregoing procedures to generate additional RB7 sequences include soybean (*Glycine max*), potato (*Solanum tuberosum*), cotton (*Gossypium hirsutum*), sugarbeet (*Beta vulgaris*), sunflower (*Helianthus annuus*), carrot (*Daucus carota*), celery (*apium graveolens*), flax (*Linum usitatissimum*), cabbage (*Brassica oleracea capitata*) and other cruciferous plants (e.g., arabidopsis, brocolli), pepper, tomato (*Lycopersicon esculentum*), citrus trees, bean, strawberry (*Fragaria spp.*), lettuce (*Lactuca sativa*), maize (*Zea mays*), alfalfa (*Medicago sativa*), oat (*Avena spp.*), wheat (*Triticum aestivum*), rice (*Oryza sativa*), barley (*Hordeum vulgare*), sorghum and canola. As noted above, RB7 sequences from other plants are those which are at least about 75 percent homologous to a 50 base segment of the Tobacco RB7 promoter capable of directing root-specific transcription of a downstream structural gene in a plant cell. By "50 base segment" is meant a continuous portion of the TobRB7 disclosed herein which is 50 nucleotides in length.

The term "operatively associated," as used herein, refers to DNA sequences on a single DNA molecule which are associated so that the function of one is affected by the other. Thus, a promoter is operatively associated with a structural gene when it is capable of affecting the expression of that structural gene (i.e., the structural gene is under the transcriptional control of the promoter). The promoter is said to be "upstream" from the structural gene, which is in turn said to be "downstream" from the promoter.

DNA constructs, or "expression cassettes," of the present invention include, 5'-3' in the direction of transcription, a promoter of the present invention, a structural gene operatively associated with the promoter, and, optionally, transcriptional and translational termination regions such as a termination signal and a polyadenylation region. All of these regulatory regions should be capable of operating in the cells of the tissue to be transformed. The 3' termination region may be derived from the same gene as the transcriptional initiation region or a different gene.

Structural genes are those portions of genes which comprise a DNA segment coding for a protein, polypeptide, or portion thereof, possibly including a ribosome binding site and/or a translational start codon, but lacking a promoter. The term can also refer to copies of a structural gene naturally found within a cell but artificially introduced. The structural gene may encode a protein not normally found in the plant cell in which the gene is introduced or in combination with the promoter to which it is operationally associated, in which case it is termed a heterologous structural gene. Genes which may be operationally associated with a promoter of the present invention for expression in a plant species may be derived from a chromosomal gene, cDNA, a synthetic gene, or combinations thereof. Genes of interest for use in plants include those affecting a wide variety of phenotypic and non-phenotypic properties. Among the phenotypic properties are enzymes which provide for resistance to stress, such as dehydration resulting from heat and salinity, herbicides, toxic metal or trace elements, or the like. Resistance may be as a result of a change in the target site, enhancement of the amount of the target protein in the host cell, the increase in one or more enzymes involved with the biosynthetic pathway to a product which protects the host against the stress, and the like. Structural genes may be obtained from prokaryotes or eukaryotes, bacteria, fungi, e.g., yeast, viruses, plants, mammals or be synthesized in whole or in part. Illustrative genes include glyphosate resistant 3-enolpyruvylphosphoshikinate synthase gene, nitrilase, genes in the proline and glutamine biosynthetic pathway, metallothioneins, etc.

The structural gene operatively associated with the promoter of the present invention may be one which codes for a protein toxic to insects, such as a *Bacillus thuringiensis* crystal protein insect toxin. A DNA sequence encoding a *B. thuringiensis* toxin toxic to Coleoptera, and variations of this sequence wherein the coded-for toxicity is retained, is disclosed in U.S. Pat. No. 4,853,331 (see also U.S. Pat. Nos. 4,918,006 and 4,910,136)(the disclosures of all U.S. Patent references cited herein are to be incorporated herein by reference). A gene sequence from *B. thuringiensis* which renders plant species toxic to Lepidoptera is disclosed in PCT Application WO 90/02804. PCT Application WO 89/04868 discloses transgenic plants transformed with a vector which promotes the expression of a *B. thuringiensis* crystal protein, the sequence of which may be employed in connection with the present invention. PCT Application WO 90/06999 discloses DNA encoding a *B. thuringiensis* crystal protein toxin active against Lepidoptera. Another gene sequence encoding an insecticidal crystal protein is disclosed in U.S. Pat. No. 4,918,006. Exemplary of gene sequences encoding other insect toxins are gene sequences encoding a chitinase (e.g., EC-3.2.1.14), as disclosed in U.S. Pat. No. 4,940,840 and PCT Appln. No. WO 90/07001.

Where the expression product of the gene is to be located in a cellular compartment other than the cytoplasm, the structural gene may be constructed to include regions which code for particular amino acid sequences which result in translocation of the product to a particular site, such as the cell plasma membrane, or may be secreted into the periplasmic space or into the external environment of the cell. Various secretory leaders, membrane integration sequences, and translocation sequences for directing the peptide expression product to a particular site are described in the literature. See, for example, Cashmore et al., Biotechnology (1985) 3:803–808, Wickner and Lodish, Science (1985) 230:400–407.

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complementation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase, providing indigo production, luciferase, providing visible light production, NPTII, providing kanamycin resistance or G418 resistance, HPT, providing hygromycin resistance, and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Maniatis et al., Molecular Cloning: A Laboratory Manual, Cold Spring Harbor Laboratory, Cold Spring Harbor, N.Y., 1982.

Vectors which may be used to transform plant tissue with DNA constructs of the present invention include both Agrobacterium vectors and ballistic vectors, as well as vectors suitable for DNA-mediated transformation.

*Agrobacterium tumefaciens* cells containing a DNA construct of the present invention, wherein the DNA construct comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous Agrobacterium vector systems useful in carrying out the present invention are known. For example, U.S. Pat. No. 4,459,355 discloses a method for transforming susceptible plants, including dicots, with an Agrobacterium strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium vector (i.e., one in which the Agrobacterium contains one plasmid having the vir region of a Ti plasmid but no T region, and a second plasmid having a T region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Agracetus European Patent Application Publication No. 0 270 356, titled *Pollen-mediated Plant Transformation*. When using ballistic transformation procedures, the expression cassette may be incorporated into a plasmid capable of replicating in the cell to be transformed. Examples of microparticles suitable for use in such systems include 1 to 5 μm gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

The promoter sequences disclosed herein may be used to express a structural gene in any plant species capable of utilizing the promoter (i.e., any plant species the RNA polymerase of which binds to the promoter sequences disclosed herein). Examples of plant species, including both monocots and dicots, are tobacco, soybean, potato, cotton, sugarbeet, sunflower, carrot, celery, flax, cabbage and other cruciferous plants, pepper, tomato, citrus trees, bean, strawberry, lettuce, maize, alfalfa, oat, wheat, rice, barley, sorghum and canola.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

The examples which follow are provided to illustrate various specific embodiments of the present invention, and are not to be construed as limiting the invention.

EXAMPLE 1

Isolation and Expression of Genomic Root-Specific Clone RB7

*Nicotiana tabacum* cv Wisconsin 38 was used as the source of material for cloning and gene characterization. Genomic DNA was partially digested with Sau3A and size-fractionated on 5 to 20% potassium acetate gradients. Size fractions of 17 to 23 kb were pooled and ligated into the λ vector, EMBL3b that had been digested with BamHI and EcoRI. See A. Frischauf et al., J. Mol. Biol. 170, 827–842 (1983). A primary library of approximately $3.5 \times 10^6$ recombinants was screened by plaque hybridization. Positive clones were plaque purified. Restriction maps of the genomic clones were constructed using the rapid mapping procedure of Rachwitz et al., Gene 30, 195–200 (1984).

Regions encoding the root-specific clones were identified by Southern blots. To further define the transcribed regions, we took advantage of the fact that the genes are expressed at high levels. Thus, probes made of cDNA of reverse transcribed poly(A+)RNA would hybridize to Southern blots of restricted genomic clones in a manner analogous to differential screening experiments. See F. Kilcherr, Nature 321, 493–499 (1986). The clones were digested with the appropriate restriction enzymes and the fragments separated on agarose gels. These fragments were then Southern blotted to nitrocellulose filters and probed with reverse transcribed root poly(A+)RNA. The probe was primed using random hexanucleotides (Pharmacia Biochemicals, Inc.) such that the 3' termini of the mRNA molecules would not be over represented among the probe.

Clones hybridizing to each root-specific cDNA clone were plaque purified. Preliminary restriction maps of some of the isolated genomic clones are shown in FIG. 1. Comparisons of the restriction maps of the genomic clones (FIG. 1) with genomic Southern hybridization experiments (not shown) reveal a good correlation of the sequences hybridizing to the root-specific cDNA clones. Clones λ5A and λ8D appear overlapping and, along with λ18C, hybridize to the cDNA clone TobRB7. All of the fragments hybridizing strongly to TobRB7 in genomic Southern hybridization experiments may be accounted for by those hybridizing from the genomic clones, suggesting that the genomic sequences encoding this cDNA have been isolated. Note that clone λ18C, though encoding a different gene from clones λ5A and λ8D, shows about 90% nucleotide sequence homology in the first 800 base pairs upstream from the structural gene.

Clone λ5A was designated as TobRB7-5A (SEQ ID NO: 1) and used to generate the promoter sequences employed in the experiments described below. This clone is hypothesized to code for a cell membrane channel protein (SEQ ID NO: 2).

EXAMPLE 2

Root-Specific Expression of an Exogenous Reporter Gene with the TobRB7 Promoter The ability of the TobRB7 promoter region of the λ5A genomic clone to regulate the expression of a heterologous reporter gene was tested by cloning approximately 1.4 kb of 5' flanking sequence into pBI101.2 In brief, a TobRB7 5' flanking region (SEQ ID NO: 3) was isolated from λ5A and fused with β-glucuronidase in the Agrobacterium binary vector, pBI 101.2. This vector contains a β-glucuronidase (GUS) reporter gene and an nptII selectable marker flanked by the T-DNA border sequences (R. Jefferson et al., EMBO J. 6, 3901–3907 (1987)). The construction was mobilized into an Agrobacterium host that carries a disarmed Ti-plasmid (LBA4404) capable of providing (in trans) the vir functions required for T-DNA transfer and integration into the plant genome, essentially as described by An et al., in S. Belvin and R. Schilperoot, eds., Plant Molecular Biology Manual, Martinus Nijhoff, Dordrecht, The Netherlands, pp A3-1-19 (1988). *Nicotiana tabacum* SR1 leaf discs were infected and transformants selected and regenerated as described by An et al., Plant Physiol. 81, 301–305 (1986). Whole plants or excised root and leaf tissue were assayed for GUS expression according to Jefferson et al., supra. For histochemical staining, plants were incubated in the 5-bromo-4-chloro-3-indolyl β-D-glucuronide (X-GLUC) at 37° C. overnight. Tissues expressing GUS activity cleave this substrate and thereby stain blue. After the incubation the tissues were bleached in 70% ethanol. GUS enzyme activities were measured using the fluorogenic assay described by Jefferson et al.

Table 1 below presents GUS activity measurements of roots and leaves from five independent transformants. Although variable expression levels are observed from transformant to transformant, in all cases GUS activity is root-specific, demonstrating that these sequences are sufficient for regulated gene expression.

TABLE 1

| Organ-Specific Expression of GUS Activity in Transgenic Plants | | |
|---|---|---|
| | GUS Activity | |
| Transgenic Plant No. | Roots | Leaves |
| | pmol MU/mg protein/min | |
| 1 | 100 | ND[a] |
| 2 | 170 | ND |
| 3 | 200 | ND |
| 4 | 100 | ND |
| 5 | 530 | ND |
| Nontransformed | ND | ND |

[a]Not detectable.

EXAMPLE 3

Deletion Analysis of the TobRB7 Promoter

These experiments were carried out in essentially the same manner as the experiments described in Example 2 above, except that (a) the length of the TobRB7 flanking region employed was varied to explore how various portions of the flanking region affected expression of GUS, and (b) the TobRB7 structural gene was completely removed and the TobRB7 flanking regions fused to the GUS initiating methionene codon.

Figure 2:
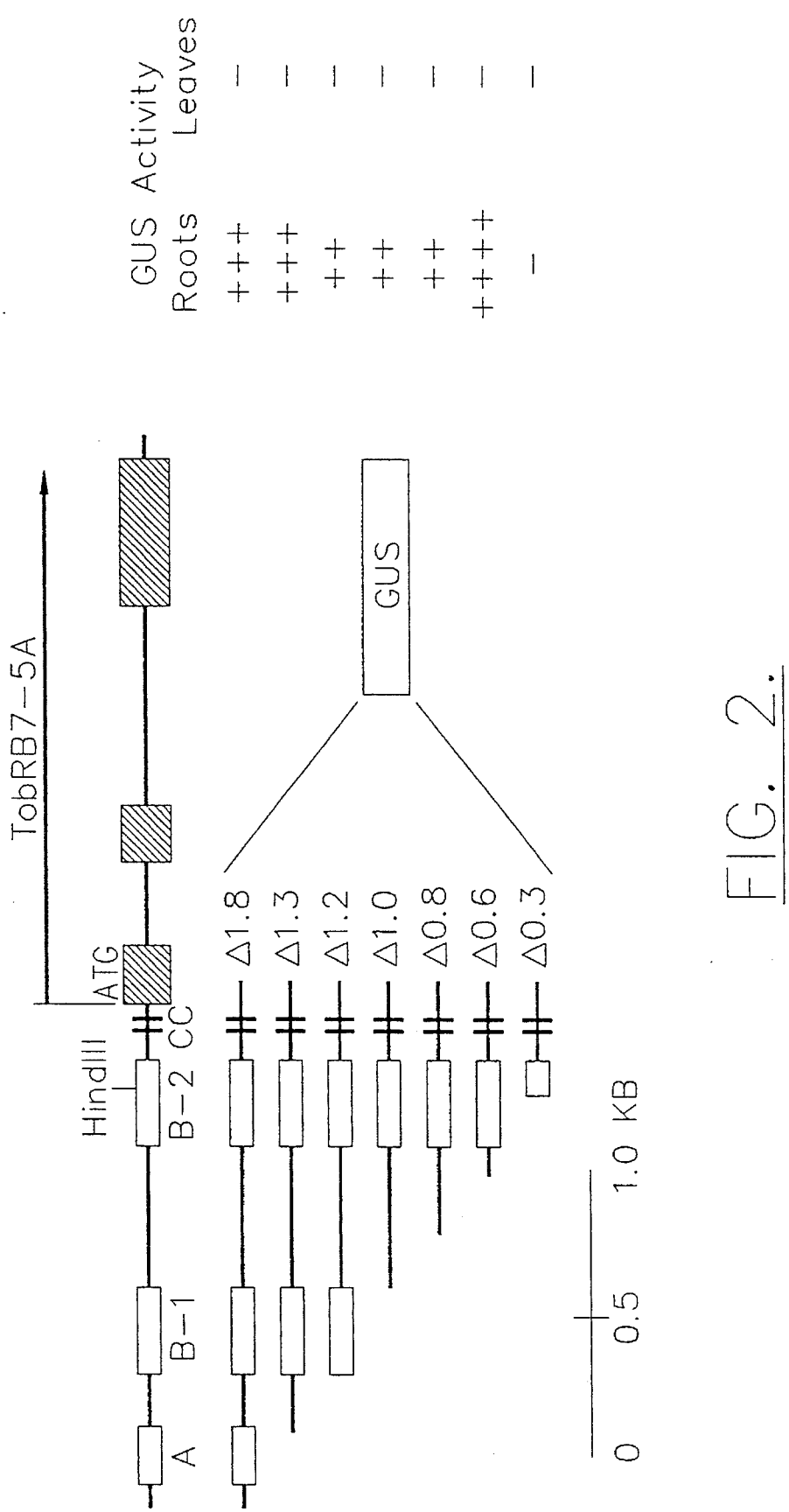
FIG. 2 schematically illustrates the deletion analysis of the genomic RB7 promoter sequence. RB7 flanking regions of various lengths where prepared and coupled to a β-Glucuronidase (GUS) gene, transgenic plants prepared with the construct, and GUS activity assayed in both the roots and the leaves of the transgenic plants. Results are summarized on the right-hand side of the Figure.

Deletion mutants employed as promoter sequences in these experiments are graphically summarized in FIG. 2. These deletion mutants are designated as Δ1.8 (SEQ ID NO:4), Δ1.3 (SEQ ID NO: 5), Δ1.2 (SEQ ID NO: 6), Δ1.0 (SEQ ID NO: 7), Δ0.8 (SEQ ID NO: 8), Δ0.6 (SEQ ID NO:9), and Δ0.3 (SEQ ID NO:10).

The activity of these various mutants is summarized in the right-hand portion of FIG. 2. Note that the greatest root-specific expression was obtained with the Δ0.6 deletion mutant, indicating the presence of an upstream silencer region. GUS activity data is presented in detail in Table 2 below. Note that only Δ0.3 (SEQ ID NO:10) was inactive as a promoter, indicating that the TobRB7 promoter is found in the region extending about 800 nucleotides upstream from the TobRB7 structural gene.

TABLE 2

| | AVERAGE GUS ACTIVITY (Range of activities) | | |
|---|---|---|---|
| | No. of Plants | ROOTS | LEAVES | Median Ratio (Roots/Leaves) |
| Wild Type | 8 | 4 (1–11) | 0.7 (0.17–2.26) | 2.8 |
| pBI–0.0 | 21 | 187 (4–614) | 6.9 (0.18–95.7) | 19.0 |
| pBI–0.3 | 21 | 160 (1–586) | 5.2 (0.8–28.4) | 21.1 |
| pBI–0.6 | 22 | 2242 (4–11,540) | 24.7 (0.05–217.5) | 122.3 |
| pBI–0.8 | 17 | 652 (2–3394) | 4.8 (0.03–23.5) | 103.2 |
| pBI–1.0 | 9 | 804 (3–2068) | 55.7 (1.72–373.4) | 97.1 |
| pBI–1.2 | 23 | 881 (2–4688) | 4.3 (0.14–22.4) | 113.5 |
| pBI–1.3 | 24 | 1475 (5–14,110) | 3.0 (0.14–8.9) | 166.4 |
| pBI–1.8 | 18 | 1007 (1–4274) | 6.5 (0.3–20.0) | 121.3 |

The foregoing examples are illustrative of the present invention, and are not to be construed as limiting thereof. The invention is defined by the following claims, with equivalents of the claims to be included therein.

That which is claimed is:

1. An isolated DNA molecule consisting essentially of a promoter which directs root-specific transcription of a downstream structural gene in a plant cell and having a sequence according to SEQ ID NO: 9.

2. A DNA construct comprising an expression cassette, which construct comprises, in the 5' to 3' direction, a promoter according to claim 1 and a structural gene positioned downstream from said promoter and operatively associated therewith wherein said promoter is flanked by sequences not naturally associated with the promoter.

3. A DNA construct according to claim 2, wherein said construct further comprises a plasmid.

4. A DNA construct according to claim 2, wherein said structural gene codes for an insect toxin.

5. A DNA construct according to claim 2, wherein said structural gene codes for a *Bacillus thuringiensis* crystal protein insect toxin.

6. A plant cell containing a DNA construct according to claim 2.

7. An *Agrobacterium tumefaciens* cell containing a DNA construct according to claim 2, and wherein said DNA construct further comprises a Ti plasmid.

8. A microparticle carrying a DNA construct according to claim 2, wherein said microparticle is suitable for the ballistic transformation of a plant cell.

9. A plant cell protoplast containing a DNA construct according to claim 2.

10. A transformed plant comprising transformed plant cells, said transformed plant cells containing a DNA construct according to claim 2.

11. A transformed plant according to claim 10, wherein said plant is a dicot.

12. A transformed plant according to claim 10, wherein said plant is a monocot.

13. A transformed plant according to claim 10, wherein said plant is a tobacco (*Nicotiana tabacum*) plant.

\* \* \* \* \*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3426 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
        ( A ) ORGANISM: Nicotiana tabacum ( v i i ) IMMEDIATE SOURCE:
        ( B ) CLONE: TobRB7-5A ( i x ) FEATURE:
        ( A ) NAME/KEY: promoter
        ( B ) LOCATION: 1..1877
        ( D ) OTHER INFORMATION:

( i x ) FEATURE:
        ( A ) NAME/KEY: CDS
        ( B ) LOCATION: join(1954..2079, 2376..2627, 2913..3284)
        ( D ) OTHER INFORMATION:

( i x ) FEATURE:
        ( A ) NAME/KEY: 5'UTR
        ( B ) LOCATION: 1878..1953
        ( D ) OTHER INFORMATION:

( x i ) SEQUENCE DESCRIPTION: SEQ ID NO:1:

```
GGATCCCCCT   CTTTTATAAT   AGAGGGTCAT   TACTTTATTT   ACAATAAAAT   AATAAAATAA     60
AGCATATAGT   GGAGGACCCA   TGATGACTTG   TTTCTTCCTC   GATTTCGCC    GAGATTCTCT    120
CCCATAGTGC   GGTTGCAACG   GCCCTTGTCT   GCGAGCTCGA   TACTGGTTCG   AGCTCGGCAT    180
TGGACCGAGC   CCTCGACCTT   GGTCCGAGCT   CGATTCTGAC   TTGGGGTCTC   GGTATTCGGG    240
GTGAGTGTTG   GTCGGTCTAT   GCATCTTCGA   TAATCTCCGT   TTTGCCTCGT   AGTTCGATTT    300
GGATATGAGC   TCGATAATGA   TACCGAGCTT   GTCATTGATC   GGTCTTAGAG   CTCGAAGTTC    360
GACGCCTTTA   CTTCGGACCT   TGACCGAGCT   TGTTATGTAG   ATATCCTTTG   ATCGAAACAT    420
TATCGTTTTG   ACCAATCCGT   ACGACTGACT   CAAATCGATT   TGACCGCACA   CAAGATTATT    480
TTCGAAAGAC   CCTCGACGTC   TTGGAGTATA   AATAATTTA    GTAAAGAGAG   TAATTGTTCG    540
TTAAAAATCT   TGACACCATT   CCAAGCATAC   CCCTTATTGT   ACTTCAATTA   ATTATCATTA    600
TATCAGCATA   AACATTATAA   TAAGTTTCTT   GCGTGTTGGA   ACGTCATTTT   AGTTATTCTA    660
AAGAGGAAAT   AGTTTCTTTT   TTGCTCATGA   CATCAGACAT   CTGGACTACT   ATACTGGAGT    720
TTACCTTTTC   TTCTCCTCTT   TTTCTTATTG   TTCCTCTAAA   AAAAATTATC   ACTTTTAAA    780
TGCATTAGTT   AAACTTATCT   CAACAACGTT   TAAAATTCAT   TTCTTGAATG   CCCATTACAA    840
TGTAATAGTA   TAACTTAATT   AGTCGTCTCC   ATGAACCATT   AATACGTACG   GAGTAATATA    900
AAACACCATT   GGGGAGTTCA   ATTTGCAATA   ATTTCTTGCA   AAAATGTAAA   GTACCTTTTT    960
GTTCTTGCAA   AATTTTACAA   ATAAAAATTT   GCAGCTCTTT   TTTTTCTCTC   TCTCCAAATA   1020
CTAGCTCAAA   ACCCACAAAT   ATTTTTGAAT   TTATGGCATA   CTTTTAGAAT   GCGTTTGATG   1080
CAACTATTTT   CCTTTAGGAA   ATATTCACAA   CAATCTAAGA   CAATCAAAAA   GTAGAAAATA   1140
GTTTGTAAAA   AGGGATGTGG   AGGACATCTT   AATCAAATAT   TTTCAGTTTA   AAACTTGAAA   1200
ATGAAAAAAC   ACCCGAAAGG   AAATGATTCG   TTCTTTAATA   TGTCCTACAC   AATGTGAATT   1260
```

| | |
|---|---:|
| TGAATTAGTT TGGTCATACG GTATATCATA TGATTATAAA TAAAAAAAAT TAGCAAAAGA | 1320 |
| ATATAATTTA TTAAATATTT TACACCATAC CAAACACAAC CGCATTATAT ATAATCTTAA | 1380 |
| TTATCATTAT CACCAGCATC AACATTATAA TGATTCCCCT ATGCGTTGGA ACGTCATTAT | 1440 |
| AGTTATTCTA AACAAGAAAG AAATTTGTTC TTGACATCAG ACATCTAGTA TTATAACTCT | 1500 |
| AGTGGAGCTT ACCTTTTCTT TTCCTTCTTT TTTTCTTCT TAAAAAAATT ATCACTTTTT | 1560 |
| AAATCTTGTA TATTAGTTAA GCTTATCTAA ACAAGTTTT AAATTCATTT CTTAAACGTC | 1620 |
| CATTACAATG TAATATAACT TAGTCGTCTC AATTAAACCA TTAATGTGAA ATATAAATCA | 1680 |
| AAAAAAGCCA AAGGGCGGTG GGACGGCGCC AATCATTTGT CCTAGTCCAC TCAAATAAGG | 1740 |
| CCCATGGTCG GCAAAACCAA ACACAAAATG TGTTATTTTT AATTTTTTCC TCTTTTATTG | 1800 |
| TTAAAGTTGC AAAATGTGTT ATTTTTGGTA AGACCCTATG GATATATAAA GACAGGTTAT | 1860 |
| GTGAAACTTG GAAAACCATC AAGTTTTAAG CAAAACCCTC TTAAGAACTT AAATTGAGCT | 1920 |

```
TCTTTTGGGG CATTTTCTA GTGAGAACTA AAA ATG GTG AGG ATT GCC TTT GGT              1974
                                    Met Val Arg Ile Ala Phe Gly
                                     1                         5

AGC ATT GGT GAC TCT TTT AGT GTT GGA TCA TTG AAG GCC TAT GTA GCT              2022
Ser Ile Gly Asp Ser Phe Ser Val Gly Ser Leu Lys Ala Tyr Val Ala
         10                  15                  20

GAG TTT ATT GCT ACT CTT CTC TTT GTG TTT GCT GGG GTT GGG TCT GCT              2070
Glu Phe Ile Ala Thr Leu Leu Phe Val Phe Ala Gly Val Gly Ser Ala
     25                  30                  35

ATA GCT TAT AGTAAGTAAC ACTTCTCTAA TTAAACTTGC ATGCTAACAT                      2119
Ile Ala Tyr
 40
```

| | |
|---|---:|
| AAATACTTAA TCTGCTCTAG CACTAAATAG TAAAAGAGC AATCAGGTGC ACTAAGGTCC | 2179 |
| CATTAATTCG TTATGCACAT GCCACGGAGT CTAGAGAAAG ACTAGACTGG CTCTATCATA | 2239 |
| TTCAATTTTA CCTTACATTT TACTAGATGC CGTTTCTCA ATCCATAACC GAAAACAACA | 2299 |
| TAACTTTTAC AGTTACACCA AGACTGCCTA ATTAACCTTT TTTTTTTTT TTTTGCTTT | 2359 |

```
GTGGGGTGAT TTTGTA GAT AAA TTG ACA GCA GAT GCA GCT CTT GAT CCA               2408
               Asp Lys Leu Thr Ala Asp Ala Ala Leu Asp Pro
                              45                  50

GCT GGT CTA GTA GCA GTA GCT GTG GCT CAT GCA TTT GCA TTG TTT GTT             2456
Ala Gly Leu Val Ala Val Ala Val Ala His Ala Phe Ala Leu Phe Val
         55                  60                  65

GGG GTT TCC ATA GCA GCC AAT ATT TCA GGT GGC CAT TTG AAT CCA GCT             2504
Gly Val Ser Ile Ala Ala Asn Ile Ser Gly Gly His Leu Asn Pro Ala
 70                  75                  80                  85

GTA ACT TTG GGA TTG GCT GTT GGT GGA AAC ATC ACC ATC TTG ACT GGC             2552
Val Thr Leu Gly Leu Ala Val Gly Gly Asn Ile Thr Ile Leu Thr Gly
             90                  95                 100

TTC TTC TAC TGG ATT GCC CAA TTG CTT GGC TCC ACA GTT GCT TGC CTC             2600
Phe Phe Tyr Trp Ile Ala Gln Leu Leu Gly Ser Thr Val Ala Cys Leu
                 105                 110                 115

CTC CTC AAA TAC GTT ACT AAT GGA TTG GTATGTACTG CTATCATTTT                   2647
Leu Leu Lys Tyr Val Thr Asn Gly Leu
             120                 125
```

| | |
|---|---:|
| CAATCCATAT TATATGTCTT TTTATATTTT TCACAACTTC AATAAAAAAA CAACTTTACC | 2707 |
| TAAGACCAGC CTAAGCCGTC GTATAGCCGT CCATCCAACC CTTTAAATTA AAAAGAGCCG | 2767 |
| GCATAGTCAT AATATATGTA TATTTCATGT AGAATATTTG TAATTAGT GTATATTGTA | 2827 |
| CGTATATCGA CTAGAAAAAA ATAAATAATG AATATGACTG TTTATTTGTA ATTGGAGTTG | 2887 |

```
GGCCTCATAT GTTGGTTTTT GGCAG GCT GTT CCA ACC CAT GGA GTT GCT GCT            2939
                              Ala Val Pro Thr His Gly Val Ala Ala
```

|  |  |  |  |  |  |  |  |  |  |  |  |  |  |  |  |
|---|---|---|---|---|---|---|---|---|---|---|---|---|---|---|---|
|  |  |  |  |  |  |  |  |  | 130 |  |  |  | 135 |  |  |
| GGG | CTC | AAT | GGA | TTA | CAA | GGA | GTG | GTG | ATG | GAG | ATA | ATC | ATA | ACC | TTT | 2987
| Gly | Leu | Asn | Gly | Leu | Gln | Gly | Val | Val | Met | Glu | Ile | Ile | Ile | Thr | Phe |
|  |  |  | 140 |  |  |  |  |  | 145 |  |  |  | 150 |  |  |
| GCA | CTG | GTC | TAC | ACT | GTT | TAT | GCA | ACA | GCA | GCA | GAC | CCT | AAA | AAG | GGC | 3035
| Ala | Leu | Val | Tyr | Thr | Val | Tyr | Ala | Thr | Ala | Ala | Asp | Pro | Lys | Lys | Gly |
|  |  |  | 155 |  |  |  |  |  | 160 |  |  |  | 165 |  |  |
| TCA | CTT | GGA | ACC | ATT | GCA | CCC | ATT | GCA | ATT | GGG | TTC | ATT | GTT | GGG | GCC | 3083
| Ser | Leu | Gly | Thr | Ile | Ala | Pro | Ile | Ala | Ile | Gly | Phe | Ile | Val | Gly | Ala |
|  |  |  | 170 |  |  |  |  |  | 175 |  |  |  | 180 |  |  |
| AAC | ATT | TTG | GCA | GCT | GGT | CCA | TTC | AGT | GGT | GGG | TCA | ATG | AAC | CCA | GCT | 3131
| Asn | Ile | Leu | Ala | Ala | Gly | Pro | Phe | Ser | Gly | Gly | Ser | Met | Asn | Pro | Ala |
|  |  |  | 185 |  |  |  |  |  | 190 |  |  |  | 195 |  |  |
| CGA | TCA | TTT | GGG | CCA | GCT | GTG | GTT | GCA | GGA | GAC | TTT | TCT | CAA | AAC | TGG | 3179
| Arg | Ser | Phe | Gly | Pro | Ala | Val | Val | Ala | Gly | Asp | Phe | Ser | Gln | Asn | Trp |
| 200 |  |  |  |  | 205 |  |  |  |  | 210 |  |  |  |  | 215 |
| ATC | TAT | TGG | GCC | GGC | CCA | CTC | ATT | GGT | GGA | GGA | TTA | GCT | GGG | TTT | ATT | 3227
| Ile | Tyr | Trp | Ala | Gly | Pro | Leu | Ile | Gly | Gly | Gly | Leu | Ala | Gly | Phe | Ile |
|  |  |  |  | 220 |  |  |  |  |  | 225 |  |  |  |  | 230 |
| TAT | GGA | GAT | GTC | TTT | ATT | GGA | TGC | CAC | ACC | CCA | CTT | CCA | ACC | TCA | GAA | 3275
| Tyr | Gly | Asp | Val | Phe | Ile | Gly | Cys | His | Thr | Pro | Leu | Pro | Thr | Ser | Glu |
|  |  |  | 235 |  |  |  |  |  | 240 |  |  |  | 245 |  |  |

```
GAC  TAT  GCT  TAAAACTTAA  AAGAAGACAA  GTCTGTCTTC  AATGTTTCTT         3324
Asp  Tyr  Ala
          250

TGTGTGTTTT  CAAATGCAAT  GTTGATTTTT  AATTTAAGCT  TTGTATATTA  TGCTATGCAA   3384

CAAGTTTGTT  TCCAATGAAA  TATCATGTTT  TGGTTTCTTT  TG                       3426
```

( 2 ) INFORMATION FOR SEQ ID NO:2:

( i ) SEQUENCE CHARACTERISTICS:
( A ) LENGTH: 250 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Val | Arg | Ile | Ala | Phe | Gly | Ser | Ile | Gly | Asp | Ser | Phe | Ser | Val | Gly |
|---|---|---|---|---|---|---|---|---|---|---|---|---|---|---|---|
| 1 |  |  |  | 5 |  |  |  |  | 10 |  |  |  |  | 15 |  |
| Ser | Leu | Lys | Ala | Tyr | Val | Ala | Glu | Phe | Ile | Ala | Thr | Leu | Leu | Phe | Val |
|  |  |  | 20 |  |  |  |  | 25 |  |  |  |  | 30 |  |  |
| Phe | Ala | Gly | Val | Gly | Ser | Ala | Ile | Ala | Tyr | Asp | Lys | Leu | Thr | Ala | Asp |
|  |  | 35 |  |  |  |  | 40 |  |  |  |  | 45 |  |  |  |
| Ala | Ala | Leu | Asp | Pro | Ala | Gly | Leu | Val | Ala | Val | Ala | Val | Ala | His | Ala |
|  | 50 |  |  |  |  | 55 |  |  |  |  | 60 |  |  |  |  |
| Phe | Ala | Leu | Phe | Val | Gly | Val | Ser | Ile | Ala | Ala | Asn | Ile | Ser | Gly | Gly |
| 65 |  |  |  |  | 70 |  |  |  |  | 75 |  |  |  |  | 80 |
| His | Leu | Asn | Pro | Ala | Val | Thr | Leu | Gly | Leu | Ala | Val | Gly | Gly | Asn | Ile |
|  |  |  |  | 85 |  |  |  |  | 90 |  |  |  |  | 95 |  |
| Thr | Ile | Leu | Thr | Gly | Phe | Phe | Tyr | Trp | Ile | Ala | Gln | Leu | Leu | Gly | Ser |
|  |  |  | 100 |  |  |  |  | 105 |  |  |  |  | 110 |  |  |
| Thr | Val | Ala | Cys | Leu | Leu | Leu | Lys | Tyr | Val | Thr | Asn | Gly | Leu | Ala | Val |
|  |  | 115 |  |  |  |  | 120 |  |  |  |  | 125 |  |  |  |
| Pro | Thr | His | Gly | Val | Ala | Ala | Gly | Leu | Asn | Gly | Leu | Gln | Gly | Val | Val |
|  | 130 |  |  |  |  | 135 |  |  |  |  | 140 |  |  |  |  |
| Met | Glu | Ile | Ile | Ile | Thr | Phe | Ala | Leu | Val | Tyr | Thr | Val | Tyr | Ala | Thr |
| 145 |  |  |  |  | 150 |  |  |  |  | 155 |  |  |  |  | 160 |

| | | | | | | | | | | | | | | |
|---|---|---|---|---|---|---|---|---|---|---|---|---|---|---|
|Ala|Ala|Asp|Pro|Lys<br>165|Lys|Gly|Ser|Leu|Gly<br>170|Thr|Ile|Ala|Pro|Ile Ala<br>175|
|Ile|Gly|Phe|Ile<br>180|Val|Gly|Ala|Asn|Ile<br>185|Leu|Ala|Ala|Gly|Pro<br>190|Phe Ser|
|Gly|Gly|Ser<br>195|Met|Asn|Pro|Ala|Arg<br>200|Ser|Phe|Gly|Pro|Ala<br>205|Val|Val Ala|
|Gly|Asp<br>210|Phe|Ser|Gln|Asn|Trp<br>215|Ile|Tyr|Trp|Ala|Gly<br>220|Pro|Leu|Ile Gly|
|Gly<br>225|Gly|Leu|Ala|Gly|Phe<br>230|Ile|Tyr|Gly|Asp|Val<br>235|Phe|Ile|Gly|Cys His<br>240|
|Thr|Pro|Leu|Pro|Thr<br>245|Ser|Glu|Asp|Tyr|Ala<br>250| | | | | |

( 2 ) INFORMATION FOR SEQ ID NO:3:

( i ) SEQUENCE CHARACTERISTICS:
        ( A ) LENGTH: 1933 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
|CCCATATGAA|AGACCCTCGA|CGTCTTGGAG|TATAAAATAA|TTTAGTAAAG|AGAGTAATTG|60|
|TTCGTTAAAA|ATCTTGACAC|CATTCCAAGC|ATACCCCTTA|TTGTACTTCA|ATTAATTATC|120|
|ATTATATCAG|CATAAACATT|ATAATAAGTT|TCTTGCGTGT|TGGAACGTCA|TTTTAGTTAT|180|
|TCTAAAGAGG|AAATAGTTTC|TTTTTTGCTC|ATGACATCAG|ACATCTGGAC|TACTATACTG|240|
|GAGTTTACCT|TTTCTTCTCC|TCTTTTTCTT|ATTGTTCCTC|TAAAAAAAAT|TATCACTTTT|300|
|TAAATGCATT|AGTTAAACTT|ATCTCAACAA|CGTTTAAAAT|TCATTCTTG|AATGCCCATT|360|
|ACAATGTAAT|AGTATAACTT|AATTAGTCGT|CTCCATGAAC|CATTAATACG|TACGGAGTAA|420|
|TATAAAACAC|CATTGGGGAG|TTCAATTTGC|AATAATTTCT|TGCAAAAATG|TAAAGTACCT|480|
|TTTTGTTCTT|GCAAAATTTT|ACAAATAAAA|ATTTGCAGCT|CTTTTTTTC|TCTCTCTCCA|540|
|AATACTAGCT|CAAAACCCAC|AAATATTTTT|GAATTATGG|CATACTTTTA|GAATGCGTTT|600|
|GATGCAACTA|TTTTCCTTTA|GGAAATATTC|ACAACAATCT|AAGACAATCA|AAAAGTAGAA|660|
|AATAGTTTGT|AAAAAGGGAT|GTGGAGGACA|TCTTAATCAA|ATATTTTCAG|TTTAAAACTT|720|
|GAAAATGAAA|AAACACCCGA|AAGGAAATGA|TTCGTTCTTT|AATATGTCCT|ACACAATGTG|780|
|AATTTGAATT|AGTTGGTCA|TACGGTATAT|CATATGATTA|TAAATAAAAA|AAATTAGCAA|840|
|AAGAATATAA|TTTATTAAAT|ATTTACACC|ATACCAAACA|CAACCGCATT|ATATATAATC|900|
|TTAATTATCA|TTATCACCAG|CATCAACATT|ATAATGATTC|CCCTATGCGT|TGGAACGTCA|960|
|TTATAGTTAT|TCTAAACAAG|AAAGAAATTT|GTTCTTGACA|TCAGACATCT|AGTATTATAA|1020|
|CTCTAGTGGA|GCTTACCTTT|TCTTTTCCTT|CTTTTTTTC|TTCTTAAAAA|AATTATCACT|1080|
|TTTTAAATCT|TGTATATTAG|TTAAGCTTAT|CTAAACAAAG|TTTTAAATTC|ATTTCTTAAA|1140|
|CGTCCATTAC|AATGTAATAT|AACTTAGTCG|TCTCAATTAA|ACCATTAATG|TGAAATATAA|1200|
|ATCAAAAAAA|GCCAAGGGC|GGTGGGACGG|CGCCAATCAT|TTGTCCTAGT|CCACTCAAAT|1260|
|AAGGCCCATG|GTCGGCAAAA|CCAAACACAA|AATGTGTTAT|TTTTAATTTT|TTCCTCTTTT|1320|
|ATTGTTAAAG|TTGCAAAATG|TGTTATTTTT|GGTAAGACCC|TATGGATATA|TAAAGACAGG|1380|
|TTATGTGAAA|CTTGGAAAAC|CATCAAGTTT|TAAGCAAAAC|CCTCTTAAGA|ACTTAAATTG|1440|
|AGCTTCTTTT|GGGGCATTTT|TCTAGTGAGA|ACTAAAAATG|GTGAGGATTG|CCTTTGGTAG|1500|

|  |  |  |  |  |  |
|---|---|---|---|---|---|
| CATTGGTGAC | TCTTTTAGTG | TTGGATCATT | GAAGGCCTAT | GTAGCTGAGT | TTATTGCTAC | 1560 |
| TCTTCTCTTT | GTGTTTGCTG | GGGTTGGGTC | TGCTATAGCT | TATAGTAAGT | AACACTTCTC | 1620 |
| TAATTAAACT | TGCATGCTAA | CATAAATACT | TAATCTGCTC | TAGCACTAAA | TAGTAAAAAG | 1680 |
| AGCAATCAGG | TGCACTAAGG | TCCCATTAAT | TCGTTATGCA | CATGCCACGG | AGTCTAGAGA | 1740 |
| AAGACTAGAC | TGGCTCTATC | ATATTCAATT | TTACCTTACA | TTTTACTAGA | TGCCGTTTTC | 1800 |
| TCAATCCATA | ACCGAAAACA | ACATAACTTT | TACAGTTACA | CCAAGACTGC | CTAATTAACC | 1860 |
| TTTTTTTTTT | TTTTTTTTGC | TTTGTGGGGT | GATTTGTAG | ATAAATTGAC | AGCAGATGCA | 1920 |
| GCTCTTGATC | CAG |  |  |  |  | 1933 |

( 2 ) INFORMATION FOR SEQ ID NO:4:

( i ) SEQUENCE CHARACTERISTICS:
        ( A ) LENGTH: 1859 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

|  |  |  |  |  |  |
|---|---|---|---|---|---|
| CCCATATTCC | TCGATTTTCG | CCGAGATTCT | CTCCCATAGT | GCGGTTGCAA | CGGCCCTTGT | 60 |
| CTGCGAGCTC | GATACTGGTT | CGAGCTCGGC | ATTGGACCGA | GCCCTCGACC | TTGGTCCGAG | 120 |
| CTCGATTCTG | ACTTGGGGTC | TCGGTATTCG | GGGTGAGTGT | TGGTCGGTCT | ATGCATCTTC | 180 |
| GATAATCTCC | GTTTTGCCTC | GTAGTTCGAT | TTGGATATGA | GCTCGATAAT | GATACCGAGC | 240 |
| TTGTCATTGA | TCGGTCTTAG | AGCTCGAAGT | TCGACGCCTT | TACTTCGGAC | CTTGACCGAG | 300 |
| CTTGTTATGT | AGATATCCTT | TGATCGAAAC | ATTATCGTTT | TGACCAATCC | GTACGACTGA | 360 |
| CTCAAATCGA | TTTGACCGCA | CACAAGATTA | TTTTCGAAAG | ACCCTCGACG | TCTTGGAGTA | 420 |
| TAAAATAATT | TAGTAAAGAG | AGTAATTGTT | CGTTAAAAAT | CTTGACACCA | TTCCAAGCAT | 480 |
| ACCCCTTATT | GTACTTCAAT | TAATTATCAT | TATATCAGCA | TAAACATTAT | AATAAGTTTC | 540 |
| TTGCGTGTTG | GAACGTCATT | TTAGTTATTC | TAAAGAGGAA | ATAGTTTCTT | TTTTGCTCAT | 600 |
| GACATCAGAC | ATCTGGACTA | CTATACTGGA | GTTTACCTTT | TCTTCTCCTC | TTTTTCTTAT | 660 |
| TGTTCCTCTA | AAAAAAATTA | TCACTTTTA | AATGCATTAG | TTAAACTTAT | CTCAACAACG | 720 |
| TTTAAAATTC | ATTTCTTGAA | TGCCCATTAC | AATGTAATAG | TATAACTTAA | TTAGTCGTCT | 780 |
| CCATGAACCA | TTAATACGTA | CGGAGTAATA | TAAAACACCA | TTGGGGAGTT | CAATTTGCAA | 840 |
| TAATTTCTTG | CAAAAATGTA | AAGTACCTTT | TTGTTCTTGC | AAAATTTTAC | AAATAAAAAT | 900 |
| TTGCAGCTCT | TTTTTTTCTC | TCTCTCCAAA | TACTAGCTCA | AAACCCACAA | ATATTTTGA | 960 |
| ATTTATGGCA | TACTTTTAGA | ATGCGTTTGA | TGCAACTATT | TTCCTTTAGG | AAATATTCAC | 1020 |
| AACAATCTAA | GACAATCAAA | AAGTAGAAAA | TAGTTTGTAA | AAAGGGATGT | GGAGGACATC | 1080 |
| TTAATCAAAT | ATTTTCAGTT | TAAAACTTGA | AAATGAAAAA | ACACCCGAAA | GGAAATGATT | 1140 |
| CGTTCTTTAA | TATGTCCTAC | ACAATGTGAA | TTTGAATTAG | TTTGGTCATA | CGGTATATCA | 1200 |
| TATGATTATA | AATAAAAAAA | ATTAGCAAAA | GAATATAATT | TATTAAATAT | TTTACACCAT | 1260 |
| ACCAAACACA | ACCGCATTAT | ATATAATCTT | AATTATCATT | ATCACCAGCA | TCAACATTAT | 1320 |
| AATGATTCCC | CTATGCGTTG | GAACGTCATT | ATAGTTATTC | TAAACAAGAA | AGAAATTTGT | 1380 |
| TCTTGACATC | AGACATCTAG | TATTATAACT | CTAGTGGAGC | TTACCTTTTC | TTTTCCTTCT | 1440 |
| TTTTTTTCTT | CTTAAAAAAA | TTATCACTTT | TTAAATCTTG | TATATTAGTT | AAGCTTATCT | 1500 |

| | | | | | |
|---|---|---|---|---|---|
| AAACAAAGTT | TTAAATTCAT | TTCTTAAACG | TCCATTACAA | TGTAATATAA | CTTAGTCGTC | 1560 |
| TCAATTAAAC | CATTAATGTG | AAATATAAAT | CAAAAAAGC | CAAAGGGCGG | TGGGACGGCG | 1620 |
| CCAATCATTT | GTCCTAGTCC | ACTCAAATAA | GGCCCATGGT | CGGCAAAACC | AAACACAAAA | 1680 |
| TGTGTTATTT | TTAATTTTTT | CCTCTTTTAT | TGTTAAAGTT | GCAAATGTG | TTATTTTGG | 1740 |
| TAAGACCCTA | TGGATATATA | AAGACAGGTT | ATGTGAAACT | TGGAAAACCA | TCAAGTTTTA | 1800 |
| AGCAAAACCC | TCTTAAGAAC | TTAAATTGAG | CTTCTTTTGG | GGCATTTTC | TAGTGAGAA | 1859 |

( 2 ) INFORMATION FOR SEQ ID NO:5:

( i ) SEQUENCE CHARACTERISTICS:
        ( A ) LENGTH: 1385 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| CCCATATCCC | CTTATTGTAC | TTCAATTAAT | TATCATTATA | TCAGCATAAA | CATTATAATA | 60 |
| AGTTTCTTGC | GTGTTGGAAC | GTCATTTTAG | TTATTCTAAA | GAGGAAATAG | TTTCTTTTTT | 120 |
| GCTCATGACA | TCAGACATCT | GGACTACTAT | ACTGGAGTTT | ACCTTTCTT | CTCCTCTTTT | 180 |
| TCTTATTGTT | CCTCTAAAAA | AAATTATCAC | TTTTTAAATG | CATTAGTTAA | ACTTATCTCA | 240 |
| ACAACGTTTA | AAATTCATTT | CTTGAATGCC | CATTACAATG | TAATAGTATA | ACTTAATTAG | 300 |
| TCGTCTCCAT | GAACCATTAA | TACGTACGGA | GTAATATAAA | ACACCATTGG | GGAGTTCAAT | 360 |
| TTGCAATAAT | TTCTTGCAAA | AATGTAAAGT | ACCTTTTGT | TCTTGCAAAA | TTTTACAAAT | 420 |
| AAAAATTTGC | AGCTCTTTTT | TTTCTCTCTC | TCCAAATACT | AGCTCAAAAC | CCACAAATAT | 480 |
| TTTTGAATTT | ATGGCATACT | TTTAGAATGC | GTTGATGCA | ACTATTTCC | TTTAGGAAAT | 540 |
| ATTCACAACA | ATCTAAGACA | ATCAAAAAGT | AGAAAATAGT | TTGTAAAAAG | GATGTGGAG | 600 |
| GACATCTTAA | TCAAATATTT | TCAGTTTAAA | ACTTGAAAAT | GAAAAAACAC | CCGAAAGGAA | 660 |
| ATGATTCGTT | CTTTAATATG | TCCTACACAA | TGTGAATTTG | AATTAGTTTG | GTCATACGGT | 720 |
| ATATCATATG | ATTATAAATA | AAAAAAATTA | GCAAAGAAT | ATAATTTATT | AAATATTTTA | 780 |
| CACCATACCA | AACACAACCG | CATTATATAT | AATCTTAATT | ATCATTATCA | CCAGCATCAA | 840 |
| CATTATAATG | ATTCCCCTAT | GCGTTGGAAC | GTCATTATAG | TTATTCTAAA | CAAGAAAGAA | 900 |
| ATTTGTTCTT | GACATCAGAC | ATCTAGTATT | ATAACTCTAG | TGGAGCTTAC | CTTTTCTTTT | 960 |
| CCTTCTTTTT | TTTCTTCTTA | AAAAAATTAT | CACTTTTTAA | ATCTTGTATA | TTAGTTAAGC | 1020 |
| TTATCTAAAC | AAAGTTTTAA | ATTCATTTCT | TAAACGTCCA | TTACAATGTA | ATATAACTTA | 1080 |
| GTCGTCTCAA | TTAAACCATT | AATGTGAAAT | ATAAATCAAA | AAAAGCCAAA | GGGCGGTGGG | 1140 |
| ACGGCGCCAA | TCATTTGTCC | TAGTCCACTC | AAATAAGGCC | CATGGTCGGC | AAAACCAAAC | 1200 |
| ACAAAATGTG | TTATTTTTAA | TTTTTTCCTC | TTTTATTGTT | AAAGTTGCAA | AATGTGTTAT | 1260 |
| TTTTGGTAAG | ACCCTATGGA | TATATAAAGA | CAGGTTATGT | GAAACTTGGA | AAACCATCAA | 1320 |
| GTTTTAAGCA | AAACCCTCTT | AAGAACTTAA | ATTGAGCTTC | TTTTGGGGCA | TTTTTCTAGT | 1380 |
| GAGAA | | | | | | 1385 |

( 2 ) INFORMATION FOR SEQ ID NO:6:

( i ) SEQUENCE CHARACTERISTICS:
        ( A ) LENGTH: 1268 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:6:

| CCCATATATG | ACATCAGACA | TCTGGACTAC | TATACTGGAG | TTTACCTTTT | CTTCTCCTCT | 60 |
| TTTTCTTATT | GTTCCTCTAA | AAAAAATTAT | CACTTTTTAA | ATGCATTAGT | TAAACTTATC | 120 |
| TCAACAACGT | TTAAAATTCA | TTTCTTGAAT | GCCCATTACA | ATGTAATAGT | ATAACTTAAT | 180 |
| TAGTCGTCTC | CATGAACCAT | TAATACGTAC | GGAGTAATAT | AAAACACCAT | TGGGGAGTTC | 240 |
| AATTTGCAAT | AATTTCTTGC | AAAAATGTAA | AGTACCTTTT | TGTTCTTGCA | AAATTTTACA | 300 |
| AATAAAAATT | TGCAGCTCTT | TTTTTCTCT | CTCTCCAAAT | ACTAGCTCAA | AACCCACAAA | 360 |
| TATTTTTGAA | TTTATGGCAT | ACTTTTAGAA | TGCGTTTGAT | GCAACTATTT | TCCTTTAGGA | 420 |
| AATATTCACA | ACAATCTAAG | ACAATCAAAA | AGTAGAAAAT | AGTTTGTAAA | AAGGGATGTG | 480 |
| GAGGACATCT | TAATCAAATA | TTTTCAGTTT | AAAACTTGAA | AATGAAAAAA | CACCCGAAAG | 540 |
| GAAATGATTC | GTTCTTTAAT | ATGTCCTACA | CAATGTGAAT | TTGAATTAGT | TGGTCATAC | 600 |
| GGTATATCAT | ATGATTATAA | ATAAAAAAA | TTAGCAAAAG | AATATAATTT | ATTAAATATT | 660 |
| TTACACCATA | CCAAACACAA | CCGCATTATA | TATAATCTTA | ATTATCATTA | TCACCAGCAT | 720 |
| CAACATTATA | ATGATTCCCC | TATGCGTTGG | AACGTCATTA | TAGTTATTCT | AAACAAGAAA | 780 |
| GAAATTTGTT | CTTGACATCA | GACATCTAGT | ATTATAACTC | TAGTGGAGCT | TACCTTTTCT | 840 |
| TTTCCTTCTT | TTTTTCTTC | TTAAAAAAT | TATCACTTTT | TAAATCTTGT | ATATTAGTTA | 900 |
| AGCTTATCTA | AACAAAGTTT | TAAATTCATT | TCTTAAACGT | CCATTACAAT | GTAATATAAC | 960 |
| TTAGTCGTCT | CAATTAAACC | ATTAATGTGA | AATATAAATC | AAAAAAAGCC | AAAGGGCGGT | 1020 |
| GGGACGGCGC | CAATCATTTG | TCCTAGTCCA | CTCAAATAAG | GCCCATGGTC | GGCAAAACCA | 1080 |
| AACACAAAAT | GTGTTATTTT | TAATTTTTTC | CTCTTTTATT | GTTAAAGTTG | CAAAATGTGT | 1140 |
| TATTTTTGGT | AAGACCCTAT | GGATATATAA | AGACAGGTTA | TGTGAAACTT | GGAAAACCAT | 1200 |
| CAAGTTTTAA | GCAAAACCCT | CTTAAGAACT | TAAATTGAGC | TTCTTTTGGG | GCATTTTTCT | 1260 |
| AGTGAGAA | | | | | | 1268 |

( 2 ) INFORMATION FOR SEQ ID NO:7:

( i ) SEQUENCE CHARACTERISTICS:
        ( A ) LENGTH: 1100 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

| CCCATATTTA | ATTAGTCGTC | TCCATGAACC | ATTAATACGT | ACGGAGTAAT | ATAAAACACC | 60 |
| ATTGGGGAGT | TCAATTTGCA | ATAATTTCTT | GCAAAAATGT | AAAGTACCTT | TTGTTCTTG | 120 |
| CAAAATTTTA | CAAATAAAAA | TTTGCAGCTC | TTTTTTTTCT | CTCTCTCCAA | ATACTAGCTC | 180 |
| AAAACCCACA | AATATTTTTG | AATTTATGGC | ATACTTTTAG | AATGCGTTTG | ATGCAACTAT | 240 |
| TTTCCTTTAG | GAAATATTCA | CAACAATCTA | AGACAATCAA | AAAGTAGAAA | ATAGTTTGTA | 300 |
| AAAAGGGATG | TGGAGGACAT | CTTAATCAAA | TATTTTCAGT | TTAAAACTTG | AAAATGAAAA | 360 |
| AACACCCGAA | AGGAAATGAT | TCGTTCTTTA | ATATGTCCTA | CACAATGTGA | ATTTGAATTA | 420 |
| GTTGGTCAT | ACGGTATATC | ATATGATTAT | AAATAAAAAA | AATTAGCAAA | AGAATATAAT | 480 |
| TTATTAAATA | TTTTACACCA | TACCAAACAC | AACCGCATTA | TATATAATCT | TAATTATCAT | 540 |

| | | | | | |
|---|---|---|---|---|---|
| TATCACCAGC | ATCAACATTA | TAATGATTCC | CCTATGCGTT | GGAACGTCAT | TATAGTTATT | 600 |
| CTAAACAAGA | AAGAAATTTG | TTCTTGACAT | CAGACATCTA | GTATTATAAC | TCTAGTGGAG | 660 |
| CTTACCTTTT | CTTTTCCTTC | TTTTTTTTCT | TCTTAAAAAA | ATTATCACTT | TTTAAATCTT | 720 |
| GTATATTAGT | TAAGCTTATC | TAAACAAAGT | TTTAAATTCA | TTTCTTAAAC | GTCCATTACA | 780 |
| ATGTAATATA | ACTTAGTCGT | CTCAATTAAA | CCATTAATGT | GAAATATAAA | TCAAAAAAG | 840 |
| CCAAAGGGCG | GTGGGACGGC | GCCAATCATT | TGTCCTAGTC | CACTCAAATA | AGGCCCATGG | 900 |
| TCGGCAAAAC | CAAACACAAA | ATGTGTTATT | TTTAATTTTT | TCCTCTTTTA | TTGTTAAAGT | 960 |
| TGCAAAATGT | GTTATTTTTG | GTAAGACCCT | ATGGATATAT | AAAGACAGGT | TATGTGAAAC | 1020 |
| TTGGAAAACC | ATCAAGTTTT | AAGCAAAACC | CTCTTAAGAA | CTTAAATTGA | GCTTCTTTTG | 1080 |
| GGGCATTTTT | CTAGTGAGAA | | | | | 1100 |

( 2 ) INFORMATION FOR SEQ ID NO:8:

( i ) SEQUENCE CHARACTERISTICS:
        ( A ) LENGTH: 890 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

| | | | | | |
|---|---|---|---|---|---|
| CCCATATTAG | AATGCGTTTG | ATGCAACTAT | TTTCCTTTAG | GAAATATTCA | CAACAATCTA | 60 |
| AGACAATCAA | AAAGTAGAAA | ATAGTTTGTA | AAAAGGGATG | TGGAGGACAT | CTTAATCAAA | 120 |
| TATTTTCAGT | TTAAAACTTG | AAAATGAAAA | AACACCCGAA | AGGAAATGAT | TCGTTCTTTA | 180 |
| ATATGTCCTA | CACAATGTGA | ATTTGAATTA | GTTTGGTCAT | ACGGTATATC | ATATGATTAT | 240 |
| AAATAAAAAA | AATTAGCAAA | AGAATATAAT | TTATTAAATA | TTTTACACCA | TACCAAACAC | 300 |
| AACCGCATTA | TATATAATCT | TAATTATCAT | TATCACCAGC | ATCAACATTA | TAATGATTCC | 360 |
| CCTATGCGTT | GGAACGTCAT | TATAGTTATT | CTAAACAAGA | AAGAAATTTG | TTCTTGACAT | 420 |
| CAGACATCTA | GTATTATAAC | TCTAGTGGAG | CTTACCTTTT | CTTTTCCTTC | TTTTTTTCT | 480 |
| TCTTAAAAAA | ATTATCACTT | TTTAAATCTT | GTATATTAGT | TAAGCTTATC | TAAACAAAGT | 540 |
| TTTAAATTCA | TTTCTTAAAC | GTCCATTACA | ATGTAATATA | ACTTAGTCGT | CTCAATTAAA | 600 |
| CCATTAATGT | GAAATATAAA | TCAAAAAAG | CCAAAGGGCG | GTGGGACGGC | GCCAATCATT | 660 |
| TGTCCTAGTC | CACTCAAATA | AGGCCCATGG | TCGGCAAAAC | CAAACACAAA | ATGTGTTATT | 720 |
| TTTAATTTTT | TCCTCTTTTA | TTGTTAAAGT | TGCAAAATGT | GTTATTTTTG | GTAAGACCCT | 780 |
| ATGGATATAT | AAAGACAGGT | TATGTGAAAC | TTGGAAAACC | ATCAAGTTTT | AAGCAAAACC | 840 |
| CTCTTAAGAA | CTTAAATTGA | GCTTCTTTTG | GGGCATTTTT | CTAGTGAGAA | | 890 |

( 2 ) INFORMATION FOR SEQ ID NO:9:

( i ) SEQUENCE CHARACTERISTICS:
        ( A ) LENGTH: 713 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

| | | | | | |
|---|---|---|---|---|---|
| CCCATATGTC | CTACACAATG | TGAATTTGAA | TTAGTTTGGT | CATACGGTAT | ATCATATGAT | 60 |
| TATAAATAAA | AAAAATTAGC | AAAAGAATAT | AATTTATTAA | ATATTTTACA | CCATACCAAA | 120 |

```
CACAACCGCA  TTATATATAA  TCTTAATTAT  CATTATCACC  AGCATCAACA  TTATAATGAT        180

TCCCCTATGC  GTTGGAACGT  CATTATAGTT  ATTCTAAACA  AGAAAGAAAT  TTGTTCTTGA        240

CATCAGACAT  CTAGTATTAT  AACTCTAGTG  GAGCTTACCT  TTTCTTTTCC  TTCTTTTTTT        300

TCTTCTTAAA  AAAATTATCA  CTTTTTAAAT  CTTGTATATT  AGTTAAGCTT  ATCTAAACAA        360

AGTTTTAAAT  TCATTTCTTA  AACGTCCATT  ACAATGTAAT  ATAACTTAGT  CGTCTCAATT        420

AAACCATTAA  TGTGAAATAT  AAATCAAAAA  AAGCCAAAGG  GCGGTGGGAC  GGCGCCAATC        480

ATTTGTCCTA  GTCCACTCAA  ATAAGGCCCA  TGGTCGGCAA  AACCAAACAC  AAAATGTGTT        540

ATTTTTAATT  TTTTCCTCTT  TTATTGTTAA  AGTTGCAAAA  TGTGTTATTT  TTGGTAAGAC        600

CCTATGGATA  TATAAAGACA  GGTTATGTGA  AACTTGGAAA  ACCATCAAGT  TTTAAGCAAA        660

ACCCTCTTAA  GAACTTAAAT  TGAGCTTCTT  TTGGGGCATT  TTTCTAGTGA  GAA              713
```

( 2 ) INFORMATION FOR SEQ ID NO:10:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
CCCATATAGC  TTATCTAAAC  AAAGTTTTAA  ATTCATTTCT  TAAACGTCCA  TTACAATGTA         60

ATATAACTTA  GTCGTCTCAA  TTAAACCATT  AATGTGAAAT  ATAAATCAAA  AAAAGCCAAA        120

GGGCGGTGGG  ACGGCGCCAA  TCATTTGTCC  TAGTCCACTC  AAATAAGGCC  CATGGTCGGC        180

AAAACCAAAC  ACAAAATGTG  TTATTTTTAA  TTTTTTCCTC  TTTTATTGTT  AAAGTTGCAA        240

AATGTGTTAT  TTTTGGTAAG  ACCCTATGGA  TATATAAAGA  CAGGTTATGT  GAAACTTGGA        300

AAACCATCAA  GTTTTAAGCA  AAACCCTCTT  AAGAACTTAA  ATTGAGCTTC  TTTTGGGGCA        360

TTTTTCTAGT  GAGAA                                                            375
```